US00PP17417P2

(12) United States Plant Patent
de Bont

(10) Patent No.: US PP17,417 P2
(45) Date of Patent: Feb. 13, 2007

(54) ***AGERATUM* PLANT NAMED 'SAGE85015'**

(50) Latin Name: *Ageratum houstonianum*
Varietal Denomination: Sage85015

(75) Inventor: Diony de Bont, Alphen aan den Rijn (NL)

(73) Assignee: Paul Ecke Ranch, Encinitas, CA (US)

( * ) Notice: Subject to any disclaimer, the term of this patent is extended or adjusted under 35 U.S.C. 154(b) by 27 days.

(21) Appl. No.: 11/146,230

(22) Filed: Jun. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP15,627 P3 * 3/2005 Sanders ..... Plt./263

OTHER PUBLICATIONS http://www.copf.org/plant.asp?PIN=4423.*

* cited by examiner

*Primary Examiner*—Wendy Haas
(74) *Attorney, Agent, or Firm*—C. A. Whealy

(57) ABSTRACT

A new and distinct cultivar of *Ageratum* plant named 'Sage85015', characterized by its tall, upright and mounded plant habit; freely branching habit; dense and bushy plant habit; dark green-colored leaves; very freely flowering habit with numerous inflorescences per plant; and inflorescences rayless with violet-colored disc florets.

1 Drawing Sheet

Botanical designation: *Ageratum houstonianum.*
Cultivar denomination: 'Sage85015'.

CROSS-REFERENCE TO RELATED APPLICATIONS

*Ageratum* Plant Named 'Sage00591'; Diony de Bont, Applicant; disclosed in U.S. Plant patent application Ser. No. 11/146,229.

BACKGROUND OF THE INVENTION

The present invention relates to a new and distinct cultivar of *Ageratum* plant, botanically known as *Ageratum houstonianum* and hereinafter referred to by the cultivar name 'Sage85015'.

The new *Ageratum* is a naturally-occurring whole plant mutation of the *Ageratum houstonianum* cultivar Red Top, not patented. The new *Ageratum* was discovered and selected by the Inventor as a plant within a population of plants of the cultivar Red Top in a controlled environment in Ter Aar, The Netherlands in 2001. The selection of the new *Ageratum* was based on its compact plant habit, strong plant growth, large inflorescences and attractive floret coloration.

Asexual reproduction of the new *Ageratum* by terminal cuttings in a controlled environment in Ter Aar, The Netherlands since October, 2002, has shown that the unique features of the new *Ageratum* are stable and reproduced true to type in successive generations.

SUMMARY OF THE INVENTION

The new *Ageratum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Sage85015' and distinguish the new *Ageratum* as a new and distinct cultivar:

1. Tall, upright and mounded plant habit.
2. Freely branching habit; dense and bushy plants.
3. Dark green-colored leaves.
4. Very freely flowering habit with numerous inflorescences per plant.
5. Inflorescences rayless with violet-colored disc florets.

Plants of the new *Ageratum* differ from plants of the parent, the cultivar Red Top, in the following characteristics:

1. Plants of the new *Ageratum* were more uniform than plants of the cultivar Red Top.
2. Plants of the new *Ageratum* had larger inflorescences than plants of the cultivar Red Top.
3. Plants of the new *Ageratum* and the cultivar Red Top differed in disc floret coloration.

Plants of the new *Ageratum* differ from plants of the cultivar Sage00591, disclosed in U.S. Plant patent application Ser. No. 11/146,229, primarily in disc floret coloration.

Plants of the new *Ageratum* can be compared to plants of the cultivar Blue Hawaii, not patented. In side-by-side comparisons conducted in Encinitas, Calif., plants of the new *Ageratum* differed from plants of the cultivar Blue Hawaii in the following characteristics:

1. Plants of the new *Ageratum* were taller and more vigorous than plants of the cultivar Blue Hawaii.
2. Plants of the new *Ageratum* were stronger and had thicker lateral branches than plants of the cultivar Blue Hawaii.
3. Plants of the new *Ageratum* had larger inflorescences than plants of the cultivar Blue Hawaii.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Ageratum*.

The photograph at the bottom of the sheet comprises a side perspective view of a typical flowering plant of 'Sage85015' grown in a container.

The photograph at the top of the sheet comprises a close-up view of typical inflorescences of 'Sage85015'.

DETAILED BOTANICAL DESCRIPTION

The aforementioned photographs, following observations and averaged measurements describe plants grown in Encinitas, Calif., in an outdoor nursery under full sunlight during the summer and fall with day temperatures averaging 27° C. and night temperatures averaging 16° C. Plants were grown in 13-cm containers. Plants were pinched one time. Plants had been growing for about four months when the photographs and description were taken. Color references are made to The Royal Horticultural Society Colour Chart, 1995 Edition, except where general terms of ordinary dictionary significance are used.

Botanical classification: *Ageratum houstonianum* cultivar Sage85015.

Parentage: Naturally-occurring whole plant mutation of the *Ageratum houstonianum* cultivar Red Top, not patented.

Propagation:

*Type.*—Terminal vegetative cuttings.

*Time to initiate roots, summer.*—About 5 days at 21° C.

*Time to initiate roots, winter.*—About 8 days at 18° C.

*Time to product a rooted cutting, summer.*—About 14 weeks at 21° C.

*Time to produce a rooted cutting, winter.*—About 18 weeks at 18° C.

*Root description.*—Fibrous, fine; white in color.

*Rooting description.*—Freely branching; dense.

Plant description:

*General appearance.*—Inverted triangle; tall, upright and mounded plant form with dense foliage and inflorescences held above and beyond the foliage. Vigorous and strong growth habit.

*Plant height.*—About 55 cm.

*Plant width.*—About 42 cm.

*Lateral branch description.*—Quantity per plant: About five primary lateral branches; each with about two to three secondary lateral branches. Length: About 44 cm. Diameter: About 8 mm. Internode length: About 4.5 to 5 cm. Aspect: Upright to slightly outwardly spreading. Strength: Very strong. Texture: Pubescent. Color: 145B.

*Foliage description.*—Arrangement: Initially opposite becoming alternate on flowering branches; simple. Length: About 6.7 cm. Width: About 5.5 cm. Shape: Cordate. Apex: Broadly acute. Base: Cordate. Margin: Crenate. Texture, upper and lower surfaces: Sparsely pubescent. Venation pattern: Pinnate. Petiole length: About 2.4 cm. Petiole diameter: About 4 mm. Petiole texture, upper and lower surfaces: Pubescent. Color: Developing foliage, upper surface: 147A. Developing foliage, lower surface: 147B. Fully expanded foliage, upper surface: Darker than 147A; venation, 147D. Fully expanded foliage, lower surface: 147B; venation, 147D. Petiole, upper and lower surfaces: 144A.

Inflorescences description:

*Appearance/arrangement.*—Rayless inflorescences arranged in terminal and axillary cymes. Very freely flowering habit with about four cymes per lateral branch each with about twelve inflorescences. Disc florets develop acropetally on a capitulum. Inflorescences persistent.

*Flowering response.*—Under natural conditions, plants flower during the spring and summer in Southern California; plants flower continuously during this period.

*Inflorescence longevity.*—Inflorescences last about 10 to 14 days on the plant.

*Fragrance.*—None detected.

*Cyme diameter.*—About 3 to 3.5 cm.

*Cyme height.*—About 2.2 cm.

*Inflorescence size.*—Diameter: About 1.4 cm. Depth (height): About 9 mm. Receptacle height: About 5 mm. Receptacle diameter: About 4 mm.

*Inflorescence buds, at stage of showing color.*—Height: About 5 mm. Diameter: About 6 mm. Shape: Oblate. Color: Slightly more red than 79A.

*Ray florets.*—No ray florets observed.

*Disc florets.*—Quantity per inflorescence: About 104. Shape: Tubular, elongated; apex, five-pointed; base, fused. Length: About 5 mm. Diameter, apex: About 1.5 mm. Diameter, base: Less than 1 mm. Color: Immature: More red than 79A. Mature, apex: 83A. Mature, mid-section: 77D. Mature, base: 155A.

*Involucral bracts (phyllaries).*—Quantity per inflorescence: About 30 in two whorls. Length: About 4 mm. Width: About 1 mm. Shape: Linear. Apex: Acute. Base: Truncate. Margin: Entire. Texture, upper surface: Glabrous, smooth. Texture, lower surface: Pubescent. Color, upper surface: 144B. Color, lower surface: 144A.

*Pedicels.*—Strength: Strong. Aspect: Upright to about 45° from vertical. Length, terminal inflorescence: About 6 mm. Length, second inflorescence: About 6 mm. Length, third inflorescence: About 8 mm. Diameter: About 1.5 mm. Texture: Pubescent. Color: 144B.

*Reproductive organs.*—Androecium: No stamens observed. Gynoecium: Quantity per floret: One. Pistil length: About 8 mm. Stigma shape: Bifurcate. Stigma color: 79B. Style length: About 7 mm. Style color: 79C to 79D. Ovary color: 155A. Seed/fruit: Seed and fruit production has not been observed.

Disease/pest resistance: Resistance to pathogens and pests common to *Ageratums* has not been observed on plants grown under commercial conditions.

Temperature/weather tolerance: Plants of the new *Ageratum* have been observed to be tolerant to rain, wind and to temperatures from 2 to 32° C.

It is claimed:

1. A new and distinct cultivar of *Ageratum* plant named 'Sage85015', as illustrated and described.

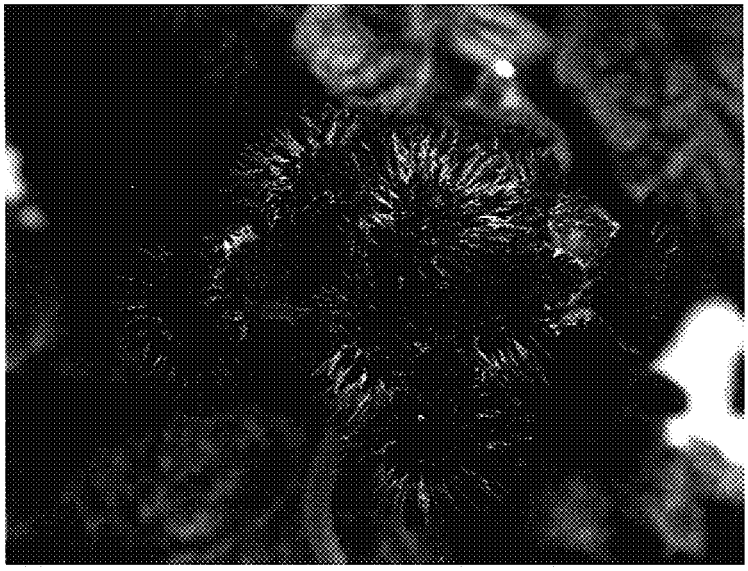
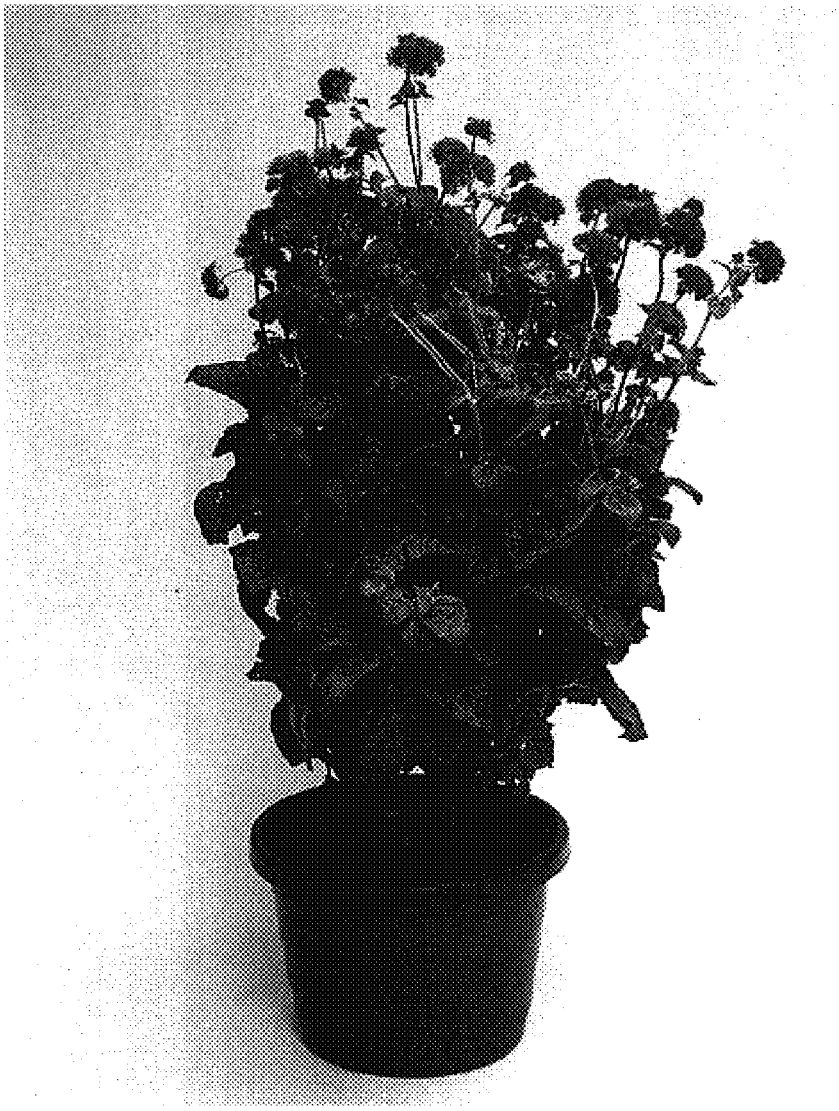

* * * * *